(12) United States Patent
Tatsumi

(10) Patent No.: US 6,509,294 B1
(45) Date of Patent: Jan. 21, 2003

(54) COMPOSITION CONTAINING BAMBOO CHARCOAL AND CARRIER HAVING THE SAME

(75) Inventor: Hiroaki Tatsumi, Osaka (JP)

(73) Assignee: Dorikamu Kabushiki Kaisha, Osaka (JP)

( * ) Notice: Subject to any disclaimer, the term of this patent is extended or adjusted under 35 U.S.C. 154(b) by 0 days.

(21) Appl. No.: 09/806,312

(22) PCT Filed: Aug. 4, 1999

(86) PCT No.: PCT/JP99/04211

§ 371 (c)(1),
(2), (4) Date: Mar. 29, 2001

(87) PCT Pub. No.: WO01/10251

PCT Pub. Date: Feb. 15, 2001

(51) Int. Cl.[7] .............................. A23L 3/00; E04B 1/00; A01N 65/00; B01J 20/22
(52) U.S. Cl. ........................ 502/401; 424/401; 424/69; 424/78.05; 426/118
(58) Field of Search ..................... 426/118, 3; 428/688; 502/401; 106/406, 474; 424/401, 69, 78.05

(56) References Cited

U.S. PATENT DOCUMENTS 6,187,324 B1 * 2/2001 Ogi et al. .................... 424/401

FOREIGN PATENT DOCUMENTS

| JP | 5-95769 | 4/1993 |
| JP | 7-126101 | 5/1995 |
| JP | 9-157064 | 6/1997 |
| JP | 9-241418 | 9/1997 |
| JP | 9-285281 | 11/1997 |
| JP | 10-277168 | 10/1998 |
| JP | 10-288100 | 10/1998 |

* cited by examiner

*Primary Examiner*—Steven Bos
*Assistant Examiner*—Anthony Kuhar
(74) *Attorney, Agent, or Firm*—Wenderoth, Lind & Ponack, L.L.P.

(57) ABSTRACT

Provided is bamboo charcoal-mixed composition 6 having an increased adsorbability in comparison with bamboo charcoal by dispersing at least bamboo charcoal powder 8 and tourmaline powder 10 into binder 14. Also provided is carrier 2 having reodorizing and antibacterial effects by holding bamboo charcoal-mixed composition 6 on base material 4 such as nonwoven fabric and pulp. Bamboo charcoal-mixed composition 6 and carrier 2 are used for various purposes such as food preservation, deodorization, antibacteria and absorption of volatile components included in building materials.

9 Claims, 1 Drawing Sheet

COMPOSITION CONTAINING BAMBOO CHARCOAL AND CARRIER HAVING THE SAME

This application is a 371 of PCT/JP99/04211 filed Aug. 4, 1999.

TECHNICAL FIELD

The present invention relates to a bamboo charcoal-mixed composition using adsorbability of bamboo charcoal and a carrier holding the composition and, furthermore, a method of using the same.

BACKGROUND ART

It has been well known that bamboo charcoal is excellent in adsorbability. This is because: bamboo charcoal is porous and has a large surface area of about 200 to 300 $m^2$ per 1 g; and the surface of bamboo charcoal exhibits an satisfactory activity of adsorption. For instance, according to the results of the analysis called BET method, the adsorbability of bamboo charcoal is about 10 times as much as that of bincho-charcoal, a representative charcoal.

Due to the high safety and excellent adsorbability of bamboo charcoal as mentioned above, a number of products using bamboo charcoal have been proposed and commercialized such as a reodorant, a product for keeping food freshness, a building product, a bedding and a health product.

However, there has been a problem that any conventional products depend only on adsorbability of bamboo charcoal. This means the conventional products have limited effects of reodorizing and keeping food freshness. Therefore, products having an increased adsorbability have been expected. For some applications, also expected have been products having an excellent antibacterial action besides the reodorizing effect.

The present invention is intended to overcome the aforementioned problem. It is therefore an object of the invention to provide an improved bamboo charcoal-mixed composition having increased adsorbability, with ensuring its safety, and a carrier holding the composition. It is another object of the invention to provide an improved bamboo charcoal-mixed composition having an excellent antibacterial action in addition to the adsorbability, and a carrier holding the composition.

DISCLOSURE OF INVENTION

According to the invention, bamboo charcoal powder and tourmaline powder are mixed and dispersed into a binder to compose a bamboo charcoal-mixed composition. The bamboo charcoal-mixed composition has an enhanced reodorizing effect in comparison with the conventional composition including only bamboo charcoal powder, because of the following reasons.

First of all, bamboo charcoal itself has sterilization, deodorization and humidity conditioning effects because of its excellent adsorbability as mentioned above. Moreover, it has been known that it can adsorb and decompose ethylene gas generated from vegetables and so on. These overall actions allow bamboo charcoal to have an effect of keeping food freshness. On the other hand, tourmaline is a silicate mineral and has pyroelectricity (i.e., it is charged with electricity by heat). It has been known that the pyroelectricity allows tourmaline to have effects including adsorbing and fixing heavy metal ions and adsorbing malodorous composition particles. Through a variety of experiments, the inventors found that mixing bamboo charcoal powder and tourmaline powder can give synergism in which the above-mentioned effects of each powder are enhanced. The inventors also found that a far infrared radiation effect of tourmaline can keep food from perishing and thereby the composition according to the present invention can be effectively used in particular for food preservation. In the present invention, bamboo charcoal is powdered in any manner to obtain the bamboo charcoal powder and tourmaline ore is powdered in any manner to obtain the tourmaline powder.

In order to obtain a satisfactory synergism, the mixing ratio of bamboo charcoal and tourmaline powders is preferably (1:0.2) to (1:5), more preferably (1:0.4) to (1:1.2) and further preferably (1:0.5) to (1:1). However, it is not limited thereto because it may be varied according to the application of the obtained composition.

The bamboo charcoal-mixed composition according to the present invention is preferably further include tannic acid, bamboo vinegar, chitosan, conker extract and/or the like, according to the application of the composition.

The inventors have studied about property of tannic acid and found that it is excellent particularly in absorbing ammonia gas. Accordingly, tannic acid is effectively added with the composition of present invention, especially in case of necessity of absorbing ammonia gas.

Bamboo vinegar is a material analogous to pyroligneous acid. It represents the upper part of the liquid obtained by cooling the gas generated in a process of dry distillation of bamboo or in a process of producing bamboo charcoal, as in pyroligneous acid (i.e., wood vinegar). It contains acetic acid and methyl alcohol in the main and, additionally, various kinds of chemical substances. The inventors found out that deodorization and mothproof actions of bamboo vinegar are extremely effective for the present invention. Moreover, when using bamboo vinegar for the present invention, the inventors found refined bamboo vinegar can exhibit deodorization and mothproof actions more efficiently, through bamboo vinegar per se can be used.

Chitosan is a material obtained from chitinous substance included in carapaces of conchostracan such as prawn and crab, and has an antibacterial action as is commonly known. Chitosan can exhibit an enhanced antibacterial action when it is combined with an acid. Therefore, in case of using for example the above-mentioned bamboo vinegar together with chitosan, the antibacterial effect of chitosan can increase by the aid of the acidity of the bamboo vinegar.

It is generally known that Conker extract, for example methanol extract of conker, exhibits a mothproof action, in particular acaricidal action. For instance, there is a data showing the survival rate of mites is below 15% after leaving the mites for 3 days on a sheet including the extract whose density of 32 $\mu m/cm^2$.

In addition, malachite green smoke powder may be added with the above-mentioned bamboo charcoal-mixed composition. The malachite green smoke powder is obtained by decocting powdery malachite green or by smoking powdery malachite green with the smoke generated in burning bamboo. The study by the inventors revealed that this malachite green smoke powder is excellent especially in adsorbing ammonia. Therefore,it may be added with the composition of the present invention instead of tannic acid. Alternatively, this malachite green smoke powder may be effectively used together with tannic acid.

As described above, by adding one or more of the above-mentioned components with the two essential components and then dispersing those components into the binder, obtained can be the bamboo charcoal-mixed composition having not only a higher adsorbability than bamboo charcoal itself but also an excellent adsorbability of ammonia gas, antibacterial property and/or the like.

In addition, the carrier according to the present invention includes a base material and the above-mentioned composition held by the base material. To prepare the bamboo charcoal-mixed composition, further components to be added with the above essential components (bamboo charcoal powder, tourmaline powder) and the respective content ratios of such components may be determined according to the application of the carrier. For example, when the carrier is a sheet mainly for food preservation, tannic acid, bamboo vinegar and/or chitosan are effectively added. Alternatively, when the carrier is a wall material or a building material sheet, especially conker extract is effectively added.

The carrier according to the present invention is not limited to such a sheet and a building material. It includes every solid material such as furniture, clothing, interior goods and toys.

BEST MODE FOR CARRYING OUT THE INVENTION

Figure 1:
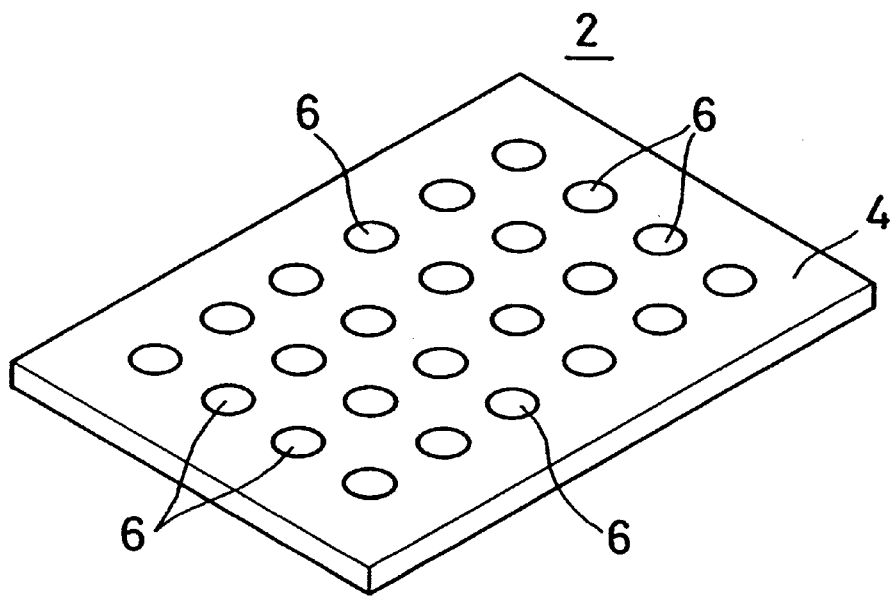
FIG. 1 is a schematic view showing an embodiment of the carrier holding the bamboo charcoal-mixed composition according to the present invention.
Figure 2:
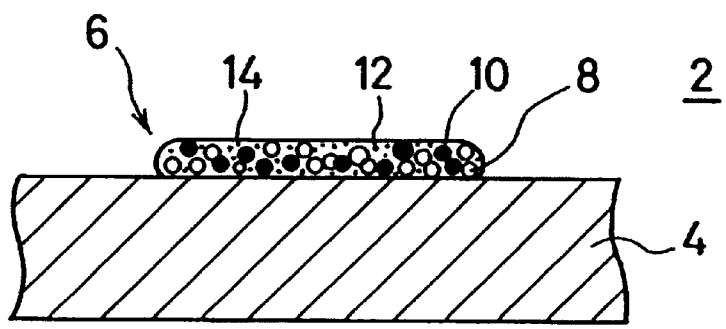
FIG. 2 is a partially enlarged view showing the carrier of FIG. 1.

An embodiment of the present invention is described by the use of FIGS. 1 and 2 in the followings. In the embodiment, the obtained carrier acts as a food preservation sheet.

Referring to FIG. 1, bamboo charcoal-mixed composition 6 is dispersed and printed on base material 4 in the form of medallion in which each circle has a diameter of about 3 mm and then dried, to obtain sheet 2.

Referring to FIG. 2, bamboo charcoal powder 8 (particle size: 5–20 $\mu$m), tourmaline powder 10 (particle size: 5–20 $\mu$m) and powdery tannic acid 12 are mixed and dispersed into sodium alginate (binder) 14 to give bamboo charcoal-mixed composition 6. Bamboo charcoal powder 8 is obtained by baking bamboo at a high temperature of more than 800° C. to give bamboo charcoal and then powdering the given bamboo charcoal. Tourmaline powder 10 is obtained by powdering tourmaline ore. Sodium alginate (binder) 14 is a water soluble sizing agent made from seaweed. As desired, bamboo vinegar and/or chitosan may be further added. The preferable amounts (weight ratio) of respective components relative to the binder (=1) are: 2 to 6 (bamboo charcoal powder 8), 1 to 6 (tourmaline powder 10), 0 to 1 (tannic acid 12), 0 to 0.5 (bamboo vinegar) and 0 to 0.5 (chitosan); and more preferably 3 to 5 (bamboo charcoal powder 8), 1.5 to 3.5 (tourmaline powder 10), 0.001 to 0.01 (tannic acid 12), 0.001 to 0.01 (bamboo vinegar) and 0.005 to 0.05 (chitosan). The thickness of bamboo charcoal-mixed composition 6 is preferably 5 to 50 $\mu$m, more preferably about 1 to 30 $\mu$m.

As the method of holding bamboo charcoal-mixed composition 6 onto base material 4, typically used may be a printing method such as screen printing, hand printing, rolling printing and gravure methods. In addition, the printed pattern on base material 4 is not limited to the circularity pattern (i.e., medallion) as seen in the embodiment. Any form may be printed thereon such as geometrical patterns including triangular and quadrangular patterns, letters and patterns of characters (for example patterns of animals). Besides printing methods, any methods may be used for holding the composition onto the base material such as painting, coating, mixing, impregnation, kneading, laminating, unweaving and interknitting. Alternatively, bamboo charcoal-mixed composition 6 may be held in between the carrier to give a so-called sandwich structure.

In order to make sure of the keeping food freshness effect of sheet 2, the following comparative experiments were conducted with using sheet 2 according to the present invention and a comparative example sheet. A leek was wrapped with sheet 2 according to the present invention. After it was left at room temperature for 100 hours, the water amount enwrapped with the sheet was measured. As a result, it was almost same as that before the 100-hour leaving. On the other hand, a leek was wrapped with the comparative example sheet and left as in the case with sheet 2. It resulted that the water amount after the 100-hour leaving was increased to about 4 times as much as that before the leaving, thereby confirming the deterioration of the leek. The similar comparative experiments were conducted with using other foods such as meat and fish. Consequently, it was confirmed that sheet 2 according to the present invention can suppress deterioration of food.

Further measured was the deodorizing ability of ammonia and trimethylamine of sheet 2 in this embodiment. It revealed that sheet 2 can decrease, for about 10 minutes, the residual ammonia density to 10% or less and the residual trimethylamine density to about 12% or less.

As described above, the sheet for keeping for freshness according to the present invention (sheet 2) is capable of adsorbing ethylene gas, the prime factor of lowering food freshness. This is because the mixture of bamboo charcoal powder 8 and tourmaline powder 10 is used to give the synergy effect of these, resulting in an excellent adsorbability. Accordingly, when a food is stored on sheet 2, the food can be kept freshly for a longer time, as compared to the case of storing the food without using sheet 2 or with using an unprocessed sheet instead. Moreover, since sheet 2 includes tannic acid 12 in addition to bamboo charcoal-powder 8 and tourmaline powder 10, it can effectively adsorb especially ammonia gas, which leads offensive odors, resulting in an excellent reodorizing effect. Sheet 2 may further have antimold and/or antibacterial effects, by adding bamboo vinegar and/or chitosan with the composition.

The term "for keeping food freshness" includes every application in spaces for storing food and cooking food. For example, the sheet for keeping food freshness can be used as a shelf paper in a refrigerator and kitchen cabinet and as a thrower and an oil screen when cooking fried food. It also can be used for storing lacquer wares.

Through sheet for keeping food freshness 2 in the above embodiment has sodium alginate 14 as the binder, any other alternatives can be used. The suitable binder, however, is sodium alginate or other natural paste (for example starch and the like), because the binder may come into contact with food directly.

In the above embodiment, in order to fix bamboo charcoal-mixed composition 6 on base material 4 such as nonwoven fabric and pulp, bamboo charcoal-mixed composition 6 is dispersed and printed on base material 4 and subsequently dried. But the method of fixing is not limited to printing, as mentioned above. It is also possible to fix bamboo charcoal-mixed composition 6 directly to the inner wall of containers for food storage such as a refrigerator and a cold-box through coating method or the like. Alternatively, bamboo charcoal-mixed composition 6 may be put in food storage containers directly or with the composition being wrapped appropriately. That is, bamboo charcoal-mixed composition 6 by itself can have the same effect as sheet 2, on which food stores. In other words, the bamboo charcoal-mixed composition according to the present invention can keep freshness of food by placing the composition near the food.

In addition, in the above-mentioned embodiment, sheet for keeping food freshness 2 is formed by fixing bamboo charcoal-mixed composition 6 on base material 4 such as nonwoven fabric and pulp, but the application of bamboo charcoal-mixed composition 6 is not limited thereto.

For instance, bamboo charcoal-mixed composition 6 may be held on any base material such as nonwoven fabric, pulp and synthetic resin, to compose a floor material for bathroom or a lavatory seat cover having a reodorizing effect. Also, it may form a reodorizing sheet available for bathroom walls and floors. In these applications, there is a particular problem of ammonia gas. Accordingly, relatively large amount of tannic acid 12 (the weight amount of tannic acid is 0.05 to 1 relative to the dispersant (=1)) is desirably used in addition to bamboo charcoal powder 8 and tourmaline powder 10 to compose bamboo charcoal-mixed composition 6. This results in more effective adsorption of ammonia gas.

Besides the above-mentioned applications, bamboo charcoal-mixed composition 6 may be used for forming a building material by printing it on ceiling and wall papers in any arbitrary patterns or by printing it on or embedding it in a sheet plate material. Alternatively, bamboo charcoal-mixed composition 6 may be coated directly on a building material such as ceiling and wall papers, sandwiched in between the building material or mixed with the building material. In these applications, this composition can be used for adsorption of various chemical substances that cause so-called sick-house sickness. In addition, bamboo charcoal-mixed composition 6 may be fixed to bedding such as futons and mats to enhance the antibacterial and reodorizing abilities of the bedding. In these applications, it is more effective to use bamboo charcoal-mixed composition 6 containing extract of conker having an acaricidal action. Since essential oil and saponin can also give the acaricidal action to the bamboo charcoal-mixed composition, they may be further added with the binder instead of or in addition to the conker extract, followed by dispersing to obtain bamboo charcoal-mixed composition 6.

Further applications include health products such as a mask in which bamboo charcoal-mixed composition 6 is fixed to fabric (for example cotton, silk or the like) or nonwoven fabric. Bamboo charcoal-mixed composition 6 is also available for clothes, underwears, socks, sock linings of shoes and the like.

As in the case of using bamboo charcoal-mixed composition 6 for keeping food freshness, bamboo charcoal-mixed composition 6 in the aforementioned various applications has the same effect in both cases that it is held by other solid material and that it is directly placed with/without being wrapped.

Industrial Applicability

According to the present invention, by dispersing at least bamboo charcoal power and tourmaline powder into the binder, it is possible to obtain an improved bamboo charcoal-mixed composition having an increased adsorbability, With ensuring its safety, and a carrier holding the composition. In addition, the adsorbability of ammonia and antibacterial ability of the bamboo charcoal-mixed composition can be enhanced by using tannic acid, bamboo vinegar, chitosan, conker extract and/or the like besides the above-mentioned two components. This makes it possible to provide carriers used for various propose such as keeping food freshness, antibacteria, deordoization and adsorption of the volatile components included in building materials.

What is claimed is:

1. A composition comprising a binder, bamboo charcoal powder and tourmaline powder, and further comprising at least one member selected from the group consisting of chitosan, bamboo vinegar, tannic acid, and extract of conker.

2. A food preservative comprising the composition according to claim 1.

3. An antibacterial agent comprising the composition according to claim 1.

4. A deodorizing agent comprising the composition according to claim 1.

5. An agent that adsorbs volatile components contained in building materials comprising the composition according to claim 1.

6. An article of manufacture comprising a base material and the composition according to claim 1.

7. The article according to claim 6, wherein the composition is printed on the base material.

8. The article according to claim 6, wherein the composition is painted on the base material.

9. The article according to claim 6, wherein the composition is mixed with the base material.

* * * * *